(12) United States Patent
Zheng et al.

(10) Patent No.: US 11,933,010 B2
(45) Date of Patent: Mar. 19, 2024

(54) METHOD AND DEVICE FOR TREATING CYANOBACTERIA IN WATER AREA BASED ON BIOLOGICAL COMPETITION PRINCIPLE

(71) Applicant: FUDAN UNIVERSITY, Shanghai (CN)

(72) Inventors: Zheng Zheng, Shanghai (CN); Weizhen Zhang, Shanghai (CN); Peng Gu, Shanghai (CN); Xingzhang Luo, Shanghai (CN); Jian He, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 491 days.

(21) Appl. No.: 17/273,425

(22) PCT Filed: Mar. 28, 2019

(86) PCT No.: PCT/CN2019/080207
§ 371 (c)(1),
(2) Date: Mar. 4, 2021

(87) PCT Pub. No.: WO2020/052221
PCT Pub. Date: Mar. 19, 2020

(65) Prior Publication Data
US 2021/0340045 A1    Nov. 4, 2021

(30) Foreign Application Priority Data

Sep. 13, 2018  (CN) .......................... 201811070277.6

(51) Int. Cl.
*E02B 3/00* (2006.01)
*C12M 1/00* (2006.01)
(Continued)

(52) U.S. Cl.
CPC ............... *E02B 3/00* (2013.01); *C12M 33/22* (2013.01); *C12M 47/02* (2013.01); *E02B 8/023* (2013.01);
(Continued)

(58) Field of Classification Search
CPC ............ E02B 3/00; E02B 8/023; E02B 15/04; C12M 33/22; C12M 47/02
See application file for complete search history.

(56) References Cited

FOREIGN PATENT DOCUMENTS

CN        103422480 A   * 12/2013

OTHER PUBLICATIONS

A Large Area Guide Enrichment Method and Device; CN 103422480 A; Wang, Shou-bing (Year: 2013).*

* cited by examiner

*Primary Examiner* — Walter D. Griffin
*Assistant Examiner* — Cameron J Allen
(74) *Attorney, Agent, or Firm* — CBM PATENT CONSULTING, LLC

(57) ABSTRACT

The invention discloses a method and a device for treating cyanobacteria in a water area based on the principle of biological competition, the method comprising: finding an area where cyanobacteria most easily accumulate, i.e. a concave bank of a water area, and setting up an algae interception net around the area; quickly and largely clearing the cyanobacteria in the area by means of manual or mechanical catching; planting emerged plants on the shoreline of the water area to fundamentally improve water quality; and additionally, densely arranging treatment tanks in a larger water area to kill the cyanobacteria gradually, and collecting dead cyanobacteria to prevent them from polluting the water area subsequently; and collecting and treating the tanks regularly for recycling.

12 Claims, 2 Drawing Sheets

(51) Int. Cl.
*C12M 1/26* (2006.01)
*E02B 8/02* (2006.01)
*E02B 15/04* (2006.01)
C02F 1/00 (2023.01)
C02F 103/00 (2006.01)

(52) U.S. Cl.
CPC ........ *E02B 15/04* (2013.01); *C02F 2001/007* (2013.01); *C02F 2103/007* (2013.01)

METHOD AND DEVICE FOR TREATING CYANOBACTERIA IN WATER AREA BASED ON BIOLOGICAL COMPETITION PRINCIPLE

TECHNICAL FIELD

The present invention relates to a method for treating cyanobacteria bloom, in particular to a method for treating cyanobacteria in water area based on the principle of biological competition, and also relates to a device for treating cyanobacteria used in the method.

BACKGROUND ART

Water bloom is attributed to the destruction of ecological balance under the condition of water eutrophication, and in China, most generally, is cyanobacteria bloom. Cyanobacteria, also known as blue-green algae, contain photosynthetic pigments such as chlorophyll a and light-harvesting pigment phycobiliprotein, and can conduct oxygenic photosynthesis. According to the difference in morphology, cyanobacteria can be divided into two groups, one is the single-cell group which usually exists as spherical and rod-shaped solitary or aggregates, and the other is the filament group which exists in the form of filamentous cell chains. Most of cyanobacteria each individually have a diameter and width of 3-10 µm. When a large number of cyanobacteria gather together, they can form visible groups. Since cyanobacteria are extremely destructive to water and toxic to humans, great efforts have to be made every year in China to clean up cyanobacteria. Many relevant departments take various treatment measures based on the local water bloom scale, characteristics and specific environment, including, for example, engineering measures such as water diversion and renewal, sediment dredging and enclosure intercepting, and chemical or biological measures using chemical reagents such as copper sulfate, permanganate, aluminum sulfate, ferrate composite chemicals and liquid chlorine, or biological agents such as cyanobacterial inhibitors.

To a certain extent, these conventional treatment methods can reduce the harm caused by cyanobacteria, but they all have their own shortcomings.

Furthermore, there are a large amount of lake algae continuously depositing to the bottom of the lake after death and decomposing subsequently, which would consume much dissolved oxygen in the deep water. In severe cases, dissolved oxygen in the deep water may be exhausted and anaerobic conditions are created thereby, making it difficult for aerobic organisms to survive, and even leading to mass deaths from suffocation of fishes in the water and consequently destroying the aquatic resources. Since the anaerobic conditions can trigger or accelerate the release of nutrients accumulated in the bottom sludge, a higher level of nutrients are loaded into the water and a vicious circle of forming eutrophic water is further created. The rotting and deteriorating of the water will eventually lead to the aging and decline of the lake. Therefore, although cyanobacteria can be killed in large quantities by some of the conventional treatment methods, the killed cyanobacteria cannot be collected in time, and the harm caused by cyanobacteria still cannot be eliminated fundamentally.

In view of the above problems, the present inventors have made a deep research on the current cyanobacteria treatment methods and developed a novel cyanobacteria treatment method based on the principle of biological competition that can overcome the defects of the prior art.

SUMMARY OF THE INVENTION

In order to overcome the above-mentioned problems, the present inventors have made a great effort to research and developed a method for treating cyanobacteria in water area based on the principle of biological competition, comprising: finding an area where cyanobacteria most easily accumulate, i.e. a concave bank of a water area, and setting up an algae interception net around the area; quickly and largely clearing the cyanobacteria in the area by means of manual or mechanical catching; planting emerged plants on the shoreline of the water area to fundamentally improve water quality; and additionally, densely arranging treatment tanks in a larger water area to kill the cyanobacteria gradually, and collecting dead cyanobacteria to prevent them from polluting the water area subsequently; and collecting and treating the tanks regularly for recycling.

Specifically, one object of the present invention is to provide a method for treating cyanobacteria in water area based on the principle of biological competition, comprising the steps of:

I: selecting an area where cyanobacteria accumulate most at a concave bank of the water area as a catching location 1, digging a sedimentation pond 2 on the shoreline, and extracting cyanobacteria from the catching location 1 to the sedimentation pond 2;

II: setting up an algae interception net 3 around the catching location 1 on the surface of the water area;

III: planting emerged plants 4 at the edge along the concave bank of the water area.

The step I further comprises the following sub-steps of:

I: finding the concave bank of the water area according to the hydrological data;

II: selecting sampling locations at predetermined intervals along the concave bank of the water area and collecting water samples at the sampling locations;

III: monitoring and analyzing the content of nitrogen and phosphorus in the water samples collected at each sampling location, and setting up catching locations on the shoreline based on the content of nitrogen and phosphorus.

Preferably, there are a plurality of the catching locations.

According to the method of the present invention, treatment tanks 5 are arranged to suspend in the waters upstream of the catching location 1, and at least a part of each tank 5 is exposed above the water surface;

algae inlet channels 6 for cyanobacteria are provided on the side wall of each treatment tank 5 close to the water surface, and the side wall below the algae inlet channels 6 is sealed;

the top of each treatment tank 5 is disposed to be open and aquatic plants are planted in the tanks 5, and the aquatic plants are local dominant species, such as emerged plants;

a railing 7 for intercepting the treatment tanks 5 is horizontally placed on the surface of the water area, so that the treatment tanks 5 are allowed to stay in a certain area of the waters;

a closable gap 8 is provided on the railing 7, and driven by the water flow, the treatment tanks 5 can sequentially pass through the gap 8;

an annular support floating ring 9 is provided around the treatment tank 5, and preferably, the inner diameter of the gap 8 is larger than the outer diameter of the support floating ring 9;

when the treatment tank 5 passes through the gap 8, the algae inlet channels 6 on the tank 5 are closed; and the treatment tanks 5 recovered downstream of the catching locations 1 are emptied and then are put back to the upstream of the catching locations 1.

The present invention also provides a device for treating cyanobacteria in water area based on the principle of biological competition, including the treatment tanks used in the method according to the present invention.

The beneficial effects of the present invention include:
(1) The method for treating cyanobacteria in waters based on the principle of biological competition according to the present invention can clean up the enriched cyanobacteria efficiently in real time, and additionally can keep cleaning cyanobacteria in a larger water area and improve the water quality by planting the emerged plants at the shore, fundamentally solving the problems caused by cyanobacteria;
(2) According to the method of the present invention, cyanobacteria are contained in the treatment tanks after killed therein, so that the further pollution caused by the dead cyanobacteria can be avoided, which is more scientific and reasonable and can significantly reduce the harm caused by cyanobacteria.

Figure 1:
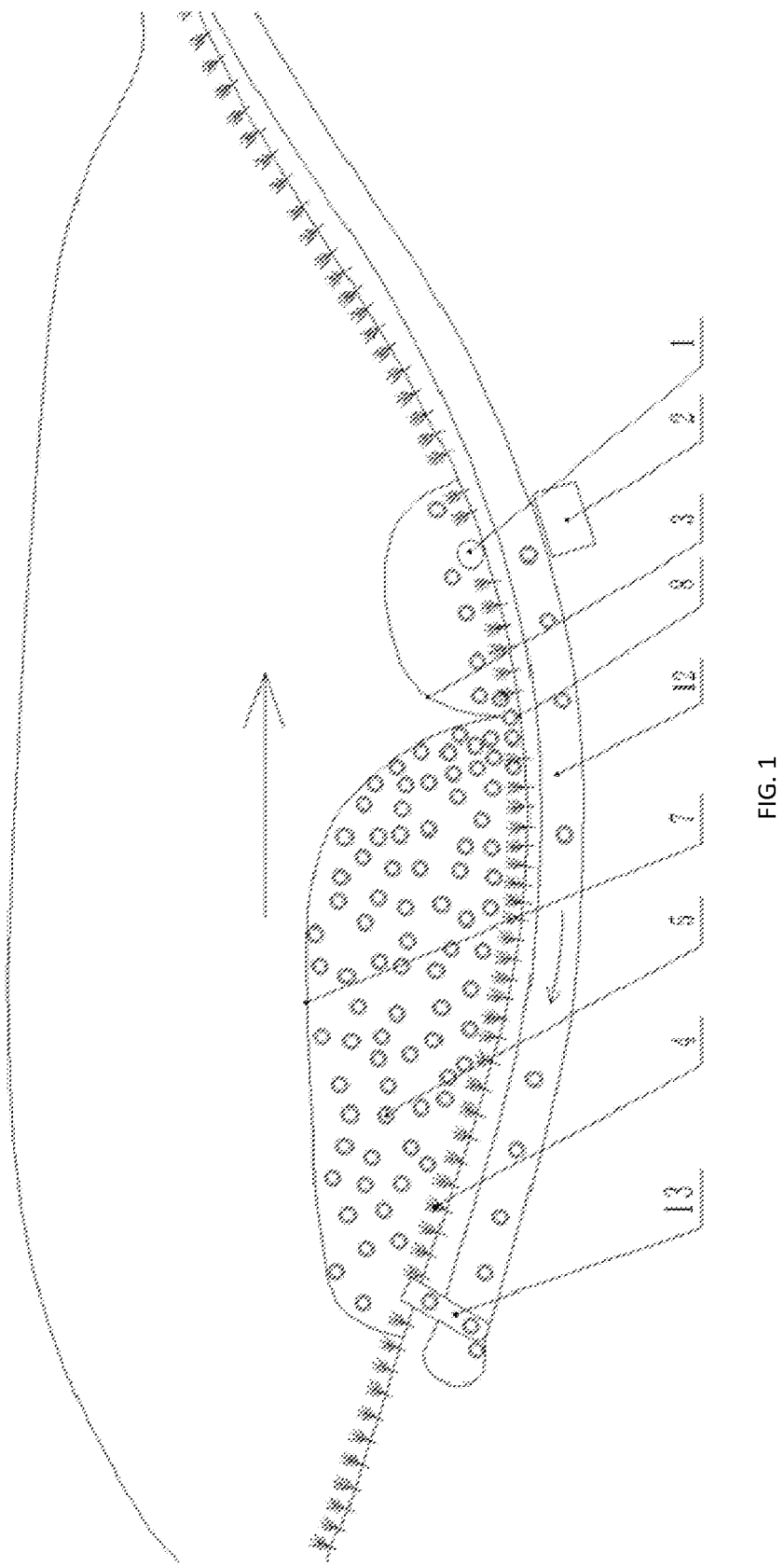
FIG. 1 shows the schematic diagram of the whole water area in the method for treating cyanobacteria in the water area according to one preferred embodiment of the present invention.

DESCRIPTION OF THE REFERENCE SIGNS catching location
sedimentation pond
algae interception net
aquatic plant
treatment tank
51—connecting bar
52—attachment bar
algae inlet channel
railing
gap
support floating ring
10—baffle door
11—connecting ring
12—water channel
13—conveyor

EMBODIMENTS

Hereinafter, the present invention will be further described in detail through the drawings and the examples. Through these descriptions, the characteristics and advantages of the present invention will become clearer.

The term "exemplary" herein means "being considered as an example, an embodiment, or an illustration." Any "exemplary" embodiment described herein should not be construed as being superior or better than other embodiments. Although various aspects of the embodiments are shown in the drawings, unless otherwise noted, the drawings are not necessarily drawn to scale.

The present invention provides a method for treating cyanobacteria in water area based on the principle of biological competition. As shown in FIG. 1, the method comprises the following steps of:

I: selecting an area where cyanobacteria accumulate most at a concave bank of the water area as a catching location 1, digging a sedimentation pond 2 on the shoreline, and extracting cyanobacteria from the catching location 1 to the sedimentation pond 2;

II: setting up an algae interception net 3 around the catching location 1 on the surface of the water area;

III: planting emerged plants 4 at the edge along the concave bank of the water area.

The waters referred in the present invention mainly include rivers, streams, lakes and other inland waters. The concave bank as used herein is a common term known to those skilled in the art. The outer bank of a curved stream, with the center of the curve toward the channel, is called the convex bank, and the inner bank opposite the convex bank is called the concave bank. When the river flows through the curved channel, under the action of centrifugal force, the surface flow deviates toward the concave bank and the bottom water flows from the concave bank to the convex bank, forming a circulation flow pattern in the curved channel, so that cyanobacteria are easily tended to accumulate at the concave bank.

According to the present invention, the operations of steps I, II and III are not performed at chronological order, and all the operations need to continue for a long time to show benefits.

The step I further comprises the following sub-steps of:

I: finding the concave bank of the water area according to the hydrological data, wherein the hydrological data includes history records for this water area, from which the diversion and erosion of the water area can be deduced;

II: selecting sampling locations at predetermined intervals along the concave bank of the water area and collecting water samples at the sampling locations, wherein the predetermined interval is preferably 5-10 meters and is required to be adjusted appropriately according to the length of the concave bank;

III: monitoring and analyzing the content of nitrogen and phosphorus in the water samples collected at each sampling location, and setting up catching locations on the shoreline based on the content of nitrogen and phosphorus, wherein there are a plurality of the catching locations arranged apart from each other in the areas where the total contents of nitrogen and phosphorus are higher.

Since the densities of cyanobacteria at the catching locations are higher, in addition to manually harvesting and transferring cyanobacteria, mechanical means, such as the catching/extracting equipment disclosed in Chinese Patent 2015205131697, A CYANOBACTERIA TREATMENT SYSTEM, can be utilized to extract cyanobacteria into the sedimentation pond.

Figure 2:
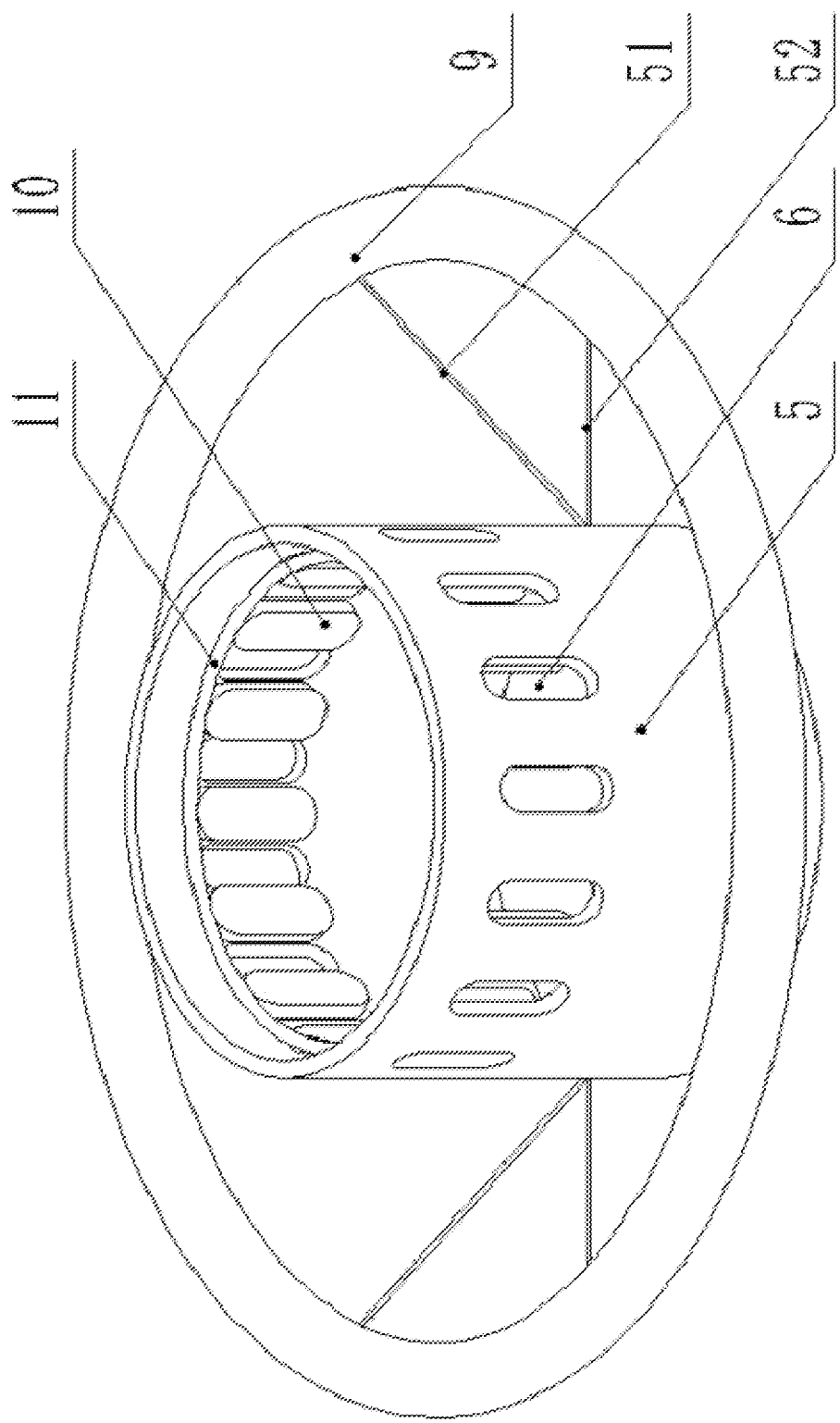
FIG. 2 shows the schematic diagram of the structure of the treatment tank used in the method for treating cyanobacteria in the water area according to one preferred embodiment of the present invention.

In one preferred embodiment, as shown in FIGS. 1 and 2, the treatment tanks 5 are arranged and suspended in the waters upstream of the catching locations 1, and at least a part of the body of each treatment tank 5 is exposed above the water surface;

algae inlet channels 6 for cyanobacteria are provided on the side wall of each treatment tank 5 close to the water surface, and the side wall below the algae inlet channels 6 is sealed.

Since most of cyanobacteria appear on the water surface layer, the treatment tanks are also disposed there, and the algae inlet channels 6 on the tank just can be contacted with cyanobacteria in the water area. Therefore, cyanobacteria can naturally enter into the treatment tank 5 and fall to the bottom of the tank 5 after killed therein, and then can be stored in the tank until the tank will be cleared. Thus, cyanobacteria killed in the treatment tank cannot pollute the waters any more.

A plurality of the treatment tanks are demanded, and the desired number of the tanks can be determined according to the area of the waters and the degree of cyanobacteria flooding. Preferably, the tanks are arranged to cover the whole water area.

In one preferred embodiment, the top of the treatment tank 5 is open, and aquatic plants are planted in the tank 5. The cyanobacteria entering the tank are killed in the biological competition with the aquatic plants, and the dead cyanobacteria accumulate in the bottom of the treatment tank. Since the side wall of the lower part of the tank is sealed, the dead cyanobacteria cannot overflow from the tank.

Preferably, the aquatic plants referred in the present invention are local dominant species, for example, emergent plants such as reed, cattail, water chestnut, lotus, cress, water bamboo, and cattail. Calamus also can be selected. According to the local situation, a plurality of dominant species with the characteristics such as easy living, pollution resistance, and developed root system can be selected in appropriate combination. For example, in the management of Dianchi Lake in China, the combination of calamus, reed, cress, etc. is determined.

In one preferred embodiment, chemical or biological agents also can be delivered into the treatment tanks to kill cyanobacteria or shorten the life of cyanobacteria.

In one preferred embodiment, as shown in FIG. 1, a railing 7 for intercepting the treatment tanks 5 is transversely arranged on the surface of the water area.

Thereby, with the railing 7, the treatment tanks 5 are allowed to stay in a specific zone of the water area. Preferably, the treatment tanks are blocked by the railing from flowing with the water, so as to stay in the specific zone of the water area for a period of time. The residence time depends on the amount of the plants or the type of the agents in the treatment tanks. Generally, the residence time takes for at most one to three days before gradually recovering the treatment tanks.

Preferably, as shown in FIG. 1, a closable gap 8 is provided on the railing 7.

Driven by the water flow, the treatment tanks 5 can pass through the gap 8 in sequence. A plurality of gaps 8 can be provided, and each gap 8 only can allow the tanks to pass through one by one, but not multiple tanks to pass through at the same time.

In one preferred embodiment, as shown in FIG. 2, an annular support floating ring 9 is provided around the treatment tank 5.

Preferably, the inner diameter of the gap 8 is larger than the outer diameter of the support floating ring 9.

Preferably, the support floating ring 9 is made of a lightweight elastic material that does not absorb water, such as a high molecular polymer. The support floating ring 9 can provide sufficient buoyancy force for the treatment tank, and can also separate the treatment tank from the adjacent tanks to avoid the treatment tanks completely covering the surface of the water area. Additionally, the support floating ring 9 can effectively prevent the treatment tank from turning over, ensuring that the tank keeps upright and cyanobacteria, especially dead cyanobacteria, in the tank cannot flow out by themselves.

In one preferred embodiment, a plurality of connecting bars 51 are provided on the treatment tank 5. One end of the connecting bar 51 is connected to the treatment tank 5, and the other end is connected to the support floating ring 9. By way of the connecting bars 51, the treatment tank 5 and the support floating ring 9 are fixed together as an integral structure.

The connecting bars 51 are located below the water surface, and submerged plants may be attached on the connecting bars 51.

Preferably, an attachment bar 52 is further provided outside the treatment tank 5. The attachment bar 52 is a thin rod and is also used for submerged plants to attach thereon. The water quality can be further purified by the submerged plants which can compress the living space of cyanobacteria by way of biological competition.

The submerged plants referred in the present invention for example include one or more of ceratophyllum, trichophyllum, utricularia, and pondweed, and can be selected as desired.

The upper part of the support floating ring 9 is above the water, and the lower part is below the water, so that cyanobacteria floating in the inner area surrounded by the support floating ring 9 are separated from those outside the ring 9. After some of cyanobacteria inside are killed, the submerged plants below the water surface can be exposed to sunlight, so as to conduct photosynthesis.

In one preferred embodiment, when the treatment tank 5 passes through the gap 8, the algae inlet channels 6 on the treatment tank 5 are closed. Since the side wall of the tank is completely sealed, no secondary pollution occurs.

Further preferably, as shown in FIG. 2, a plurality of baffle doors 10 that coordinate with the algae inlet channels 6 are provided inside the treatment tank 5 and each individually arranged between the two adjacent algae inlet channels. Preferably, the amounts of the baffle doors 10 and the algae inlet channels are same, the baffle door 10 is slightly higher and wider than the algae inlet channel 6, and the distance between the two adjacent algae inlet channels is not less than the width of the baffle door 10.

A connecting ring 11 is also provided inside the treatment tank 5 and connected with all the baffle doors 10. The connecting ring 11 is used to control the rotation or translation of the baffle doors 10, so that the baffle doors 10 can cover the algae inlet channels 6.

Further preferably, a control signal emitting device, such as an infrared emitting device, an electromagnetic signal emitting device, is provided at the gap 8 on the railing 7, and a control signal receiving device is provided on the treatment tank 5. After receiving the signal sent by the emitting device, the control signal receiving device controls the connecting ring 11 to move the baffle doors 10, so that the algae inlet channels 6 can be shielded or closed.

In one preferred embodiment, the treatment tanks 5 pass through the gap 8 and enter the catching area surrounded by the algae interception net 3 to be treated centrally. Specifically, the treatment tanks 5 are recovered in the catching area, cyanobacteria in the tanks 5 are poured into the sedimentation pond 2, and then the treatment tanks 5 are put back to the upstream of the catching location 1.

Specifically, as shown in FIG. 1, a water channel 12 is excavated on the shoreline, and water in the channel flows along the direction opposite to that in the water area. The treatment tanks 5 after cleared in the sedimentation pond 2 can be directly placed in the water channel 12 nearby. Driven by the flow in the water channel, the treatment tanks 5 can float to the upstream of the water area. In the upstream, a conveyor 13 is provided at the end of the water channel to deliver the treatment tanks 5 in the channel to the water area, and finally, the recycle of the treatment tanks 5 can be realized. Preferably, a water pump is further provided at the end of the channel to withdraw water from the channel to the water area in real time, so that water in the channel can continuously flow from the vicinity of the sedimentation pond to the upstream of the water area.

Due to the great amount of the treatment tanks 5, as soon as some of the tanks have been disposed upstream, the gaps 8 can be opened to release the tanks one by one, without detecting the content of cyanobacteria in the treatment tanks. Although the contents of cyanobacteria in the treatment tanks released at the initial stage are lower, cyanobacteria in the tanks released later will become more and more, so that the recycle of the treatment tanks can be achieved.

A switch for opening the baffle doors 10 is also provided on the treatment tank 5. After clearing cyanobacteria in the treatment tank, one can manually control the switch to move the baffle doors 10, opening the algae inlet channels 6 again.

The present invention also provides a device for treating cyanobacteria in a water area based on the principle of biological competition, comprising the treatment tanks used in the method as disclosed above according to the present invention.

In the description of the present invention, it should be noted that the terms "upper", "lower", "inner", "outer", "front" and "back" indicate the orientation or position based on the operating conditions of the present invention, which are only for the convenience of describing the present invention and simplifying the description, rather than indicating or implying that the device or element referred must be arranged, constructed or operated in a specific orientation, and therefore cannot be considered as a limitation to the present invention.

EXAMPLES

An water area with fresh water supplemented (area: 1,200,000 m², depth: 4-8 m) where cyanobacteria blooms appear every summer and no fish can survive was subjected to the cyanobacteria treatment by using the method according to the present invention. During the cyanobacteria outbreak season, the concave bank of the water area was determined according to hydrological data, and then a catching location on the concave bank was selected and a sedimentation pond on the shore near the catching location was excavated. Cyanobacteria were caught from the catching location by mechanical means and then delivered to the sedimentation pond. An algae intercepting net was arranged on the surface of the waters around the catching location. Aquatic plants were planted along the concave bank. Three to four thousands treatment tanks were arranged upstream of the catching point and continuously recycled. After two weeks of continuous treatment, the amount of cyanobacteria in the water area decreased significantly, and the color of the water changed from green to transparent. After treating continuously for a year, no cyanobacteria blooms broke out in this water area in the second year. Water in this area can satisfy the water quality requirements of Class 3, and aquaculture can be carried out in this area.

The present invention has been described in detail in combination with preferred embodiments. However, it should be noted that these embodiments are merely illustrative for the present invention and do not constitute any limitation to the scope of the present invention. Within the spirit and the scope of the present invention, various improvements, equivalent substitutions or modifications can be made to the technical content of the present invention and its embodiments, all of which fall in the scope of the present invention.

What is claimed is:

1. A method for treating cyanobacteria in a water area based on the principle of biological competition, comprising the following steps of:
   I: selecting a catching location (1) at an edge of the water area, digging a sedimentation pond (2) on a shoreline, and extracting cyanobacteria from the catching location (1) to the sedimentation pond (2);
   II: setting up an algae interception net (3) around the catching location (1) on the surface of the water area;
   III: planting emerged plants (4) at a concave bank of the water area.

2. The method according to claim 1, wherein: the step I further comprises the following sub-steps of:
   I-1: finding the concave bank of the water area according to hydrological data;
   I-2: selecting sampling locations at predetermined intervals along the concave bank of the water area and collecting water samples at the sampling locations;
   I-3: monitoring and analyzing water flow, regular wind direction, cyanobacteria density, at each sampling location, and setting up catching locations on the shoreline based on accumulation of cyanobacteria.

3. The method according to claim 2, wherein: a railing (7) for intercepting treatment tanks (5) is horizontally placed on the surface of the water area, so that the treatment tanks (5) are allowed to stay in a certain area of the water area.

4. The method according to claim 3, wherein:
   a closable gap (8) is provided on the railing (7), and driven by a water flow, the treatment tanks (5) can sequentially pass through the gap (8) and enter the catching area surrounded by the algae intercepting net (3) to be treated centrally.

5. The method according to claim 4, wherein:
   an annular support floating ring (9) is provided around the treatment tank (5).

6. The method according to claim 5, wherein the inner diameter of the gap (8) is larger than the outer diameter of the support floating ring (9).

7. The method according to claim 4, wherein:
   when the treatment tank (5) passes through the gap (8), algae inlet channels (6) on the tank (5) are closed.

8. The method according to claim 7, wherein: the cyanobacteria in the treatment tanks (5) recovered in the catching area are emptied into the sedimentation pond (2), and then the treatment tanks (5) are put back upstream of the catching location (1).

9. The method according to claim 2, wherein there are a plurality of the catching locations.

10. The method according to claim 1, wherein:
    treatment tanks (5) are arranged to be suspended in the waters upstream of the catching location (1), and at least a part of each tank (5) is exposed above the water surface;

algae inlet channels (6) for cyanobacteria are provided on a side wall of each treatment tank (5) close to the water surface, and the side wall below the algae inlet channels (6) is sealed.

11. The method according to claim 10, wherein a top of each treatment tank (5) is disposed to be open and aquatic plants are planted in the tanks (5).

12. The method according to claim 1, wherein: the aquatic emerged plants are an aquatic local dominant species.

* * * * *